United States Patent [19]

Kubo et al.

[11] Patent Number: 4,561,440

[45] Date of Patent: Dec. 31, 1985

[54] APPARATUS FOR LASER LIGHT MEDICAL TREATMENT

[75] Inventors: Kiyoshi Kubo, Katano; Toshio Ohshiro, Tokyo, both of Japan

[73] Assignees: Matsushita Electric Industrial Co., Ltd., Kadoma; Japan Medical Laser Laboratory Co., Ltd., Tokyo, both of Japan

[21] Appl. No.: 442,083

[22] Filed: Nov. 16, 1982

[30] Foreign Application Priority Data

Nov. 18, 1981 [JP] Japan ................... 56-185060
Nov. 18, 1981 [JP] Japan ................... 56-185061

[51] Int. Cl.⁴ ............................................. A61N 5/00
[52] U.S. Cl. ........................... 128/395; 219/121 LB
[58] Field of Search ........ 128/303.1, 303.13, 395–398, 128/736; 219/121 LB

[56] References Cited

U.S. PATENT DOCUMENTS

| | | | |
|---|---|---|---|
| 4,122,853 | 10/1978 | Smith | 128/303.1 |
| 4,232,678 | 11/1980 | Skevajsa | 128/395 |
| 4,279,254 | 7/1981 | Boschetti et al. | 128/395 |
| 4,295,475 | 10/1981 | Torzala | 128/736 |
| 4,303,073 | 12/1981 | Archibald | 128/303.13 |
| 4,331,161 | 5/1982 | Patel | 128/736 |
| 4,422,457 | 12/1983 | Hattori | 128/303.1 |
| 4,423,726 | 1/1984 | Imagawa et al. | 128/303.11 |
| 4,449,528 | 5/1984 | Auth et al. | 128/303.1 |

FOREIGN PATENT DOCUMENTS 2647618 10/1976 Fed. Rep. of Germany ... 128/303.1
2832847 2/1980 Fed. Rep. of Germany ... 128/303.1

Primary Examiner—Lee S. Cohen
Attorney, Agent, or Firm—Cushman, Darby & Cushman

[57] ABSTRACT

A laser light medical treatment apparatus has a contact detection means comprising a pair of contact tips 16a, 16b on both sides of a laser light emission hole 6 so that when the hand set 1, 30 of the apparatus is applied on the skin of a patient. The contact tips detect touching on the skin by means of a small conduction current thereacross, thereby closing a switching circuit 46, 44 to actuate the laser 4 to oscillate. In addition, warning sound means 8 and warning lamp means 7 are provided so as to warn of the light beam emission of the laser, which light is invisible and dangerous to the human eye.

12 Claims, 6 Drawing Figures 4,561,440

APPARATUS FOR LASER LIGHT MEDICAL TREATMENT

BACKGROUND OF THE INVENTION

Field of the Invention

The present invention relates to improvements in an apparatus for laser beam treatment. More particularly the present invention relates to improvements to avoid possible danger to human eyes by an invisible laser beam in an apparatus for laser beam treatment.

Recently, many studies of medical treatments such as acupuncture or the like have been made. And among them, treatment of various aches such as toothache, lumbago, stiffness in the shoulders arms and legs, are made by use of a laser light beam. And recently, the relations between and effects of intensity, treating time, wavelength of light and repetition period of light beam pulses on such medical treatment are more and more made clear with respect to therapeutic effect. However, causality of photochemical effect of the laser beam on medical treatment has some unclear points. Many reports have been made concerning the application of a laser beam for medical treatment. But those reports dealing with operativity and safetyness for the apparatus of such medical treatment are not yet sufficient.

The laser light beam is different from an usual light beam, in that it is coherent light which can be easily focused. Accordingly, even when using a rather small laser light beam, of for instance several milliwatts, it is possible to obtain a very high power density of the light beam by effectively converging the light beam into a very small area, for instance, from several to less than one $mm^2$. In medical treatment, usually a laser light having a wavelength range in the infrared light range is used, which is easily absorbed in human skin. Accordingly, when such invisible laser light erroneously enters human eyes because of a misoperation, then the retina of the eye may be easily destroyed to make the patient blind.

SUMMARY OF THE INVENTION

Therefore, the purpose of the present invention is to provide an improved apparatus for laser beam medical treatment, which provides increased safety measures. Also, a user is alerted to the operation of the laser light emission by a warning sound or/and a warning light. The safety measures prevent the, inadvertent entry of the laser light beam into the patient's eye, and further, an operation or treatment for an appropriate length of time is made easy.

DESCRIPTION OF THE PREFERRED EMBODIMENTS

Figure 1:
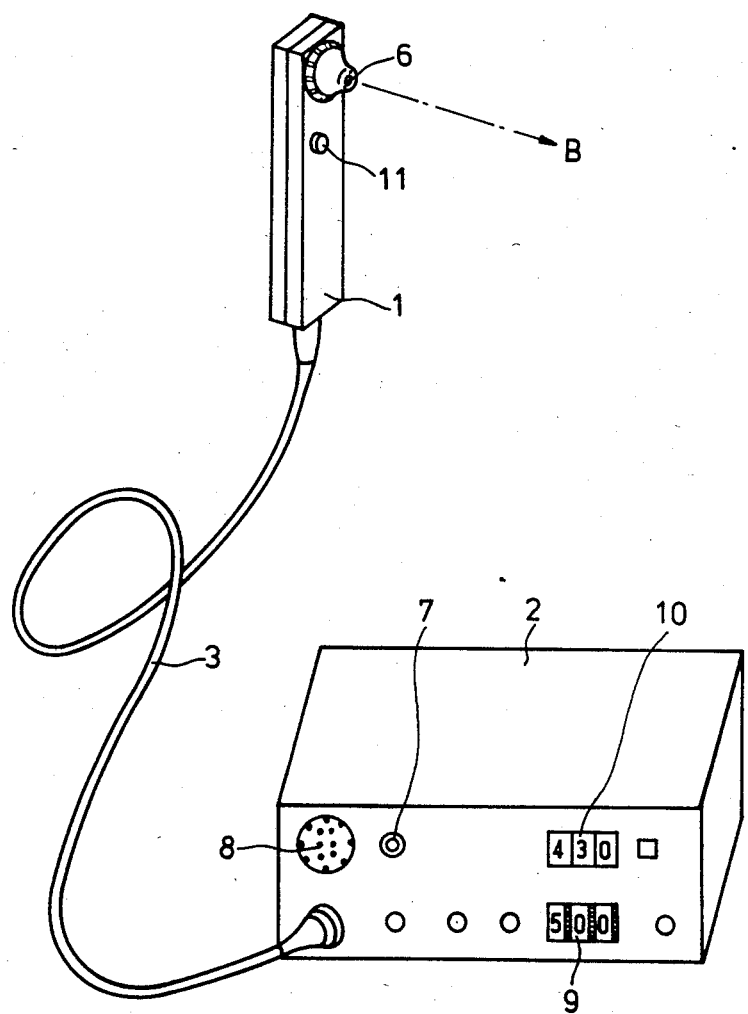
FIG. 1 is a perspective view of one example embodying the present invention.

FIG. 1 shows a general view of the apparatus for laser beam medical treatment in accordance with the present invention. The apparatus comprises a hand set 1 and a circuit part 2 and an electric cable 3 connecting the above-mentioned two parts. The hand set 1 has a laser light emitting hole 6 which is to be applied to a local point of the patient for treatment. The hand set 1 further has a switch 11 for controlling on and off of the laser light emission. The circuit part 2 has a time setting switch 9 for setting a time length for treatment and a numeral indicator 10 for indicating a set time and subsequent remaining time during treatment. The circuit part 2 further has a warning lamp 7 and small speaker 8 which are for indicating that the laser light beam is being emitted.

Figure 2:
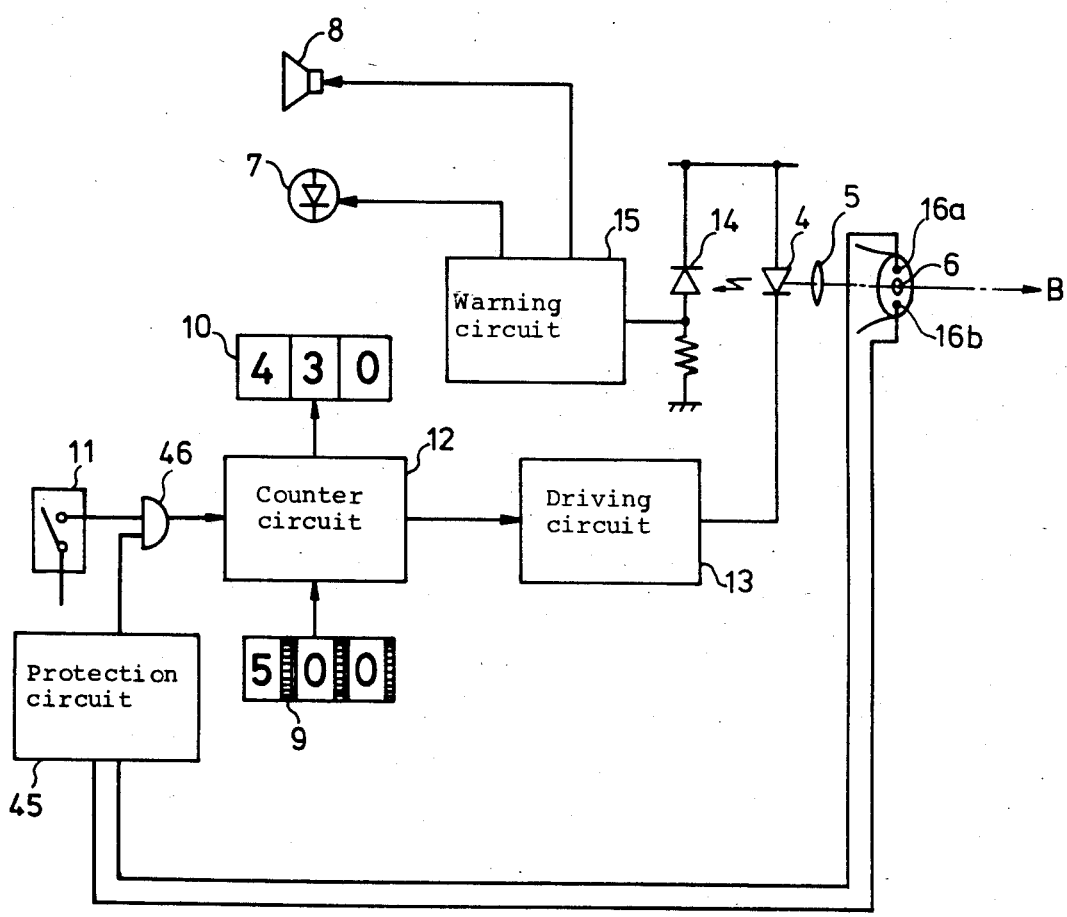
FIG. 2 is a circuit block diagram of the apparatus of FIG. 1.

FIG. 2 diagrammatically shows the connection of the apparatus of FIG. 1, wherein control switch 11 gives its outputs through an AND circuit 46, a counter circuit 12 and a driving circuit 13 which feeds laser operation current to a laser 4 which emits a light beam through a lens 5 and through emission hole 6. The time setting switch 9 gives a time set output to the counter 12 and the latter gives an output to the numeral indicator 10. A phototransistor 14 is provided to receive back light from the laser and gives its output to a warning circuit 15, which drives the warning lamp 7 and the small speaker 8.

The operation, for medical treatment, of the FIG. 2 circuit is described hereafter. At first, the user sets the time-set switch 9, for example to 5 min and 0 sec, then the set time is given to the counter 12 and the set time is indicated on the numeral indicator 10. Then by pushing the control switch 11 on the hand set 1, the control signal is given to an AND gate, which at the receipt of a signal from the protection circuit 45 gives the signal through the counter circuit 12, to the driving circuit 13, in order to actuate the laser to emit a laser light beam through the emission hole 6 of the hand set 1. As time lapses the numeral indicator 10 changes its indication thereby indicating remaining time. When the remaining time indication becomes zero, the counter 12 stops providing its output, to the driving circuit 13 and therefore the laser 4 stops emission of light. FIG. 2 shows that the numeral indicator shows 4 min and 30 sec remaining for treatment. During emission of the laser light from the emission hole 6 the a warning light 7 or/and small speaker 8 issues warning light or/and a warning sound, so that the user of the apparatus becomes careful. By means of the above numeral indicator 10 the user can accurately know the remaining time and avoid excessively long time application of the light and also feel easy by knowing the remaining time.

Figure 3:
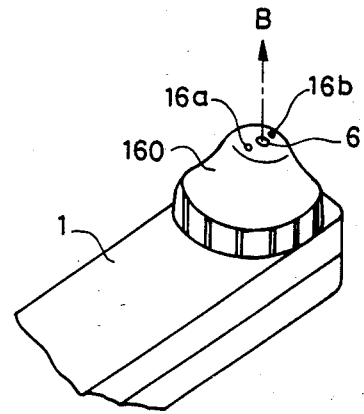
FIG. 3 is a perspective view of a hand set of the apparatus of FIG. 1.
Figure 4:
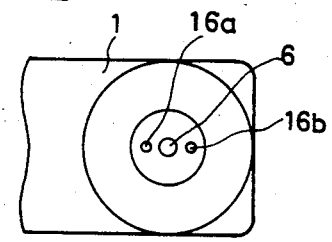
FIG. 4 is a front view of the hand set of FIG. 3.
Figure 5:
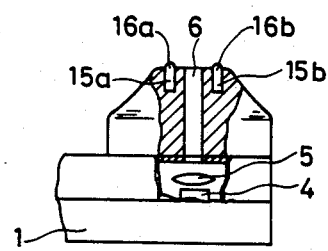
FIG. 5 is a partial sectional view of the hand set of FIG. 3.

FIG. 3 shows the detail around the light emission hole 6 of the hand set 1. On both sides of the light emission hole 6, there are provided a pair of contact tips 16a and 16b of sensor 15a and 15b, respectively as shown in FIG. 3, FIG. 4 and FIG. 5.

The contact sensor 15a and 15b are for detection of contacting or proximation of the light emission hole 6 to human skin. The sensor may be a mechanical switch, a capacitive switch or a sensor to detect minute current through electrode contacts to the human skin. In this example the sensor 15a and 15b are the electric conduction current detection means type. When the contact tips 16a and 16b touch the human skin, the protection circuit 45 issues an output to the AND gate 46, thereby allowing the counter circuit 12 to count and give its output to the driving circuit 13, thereby actuating the laser 4.

Figure 6:
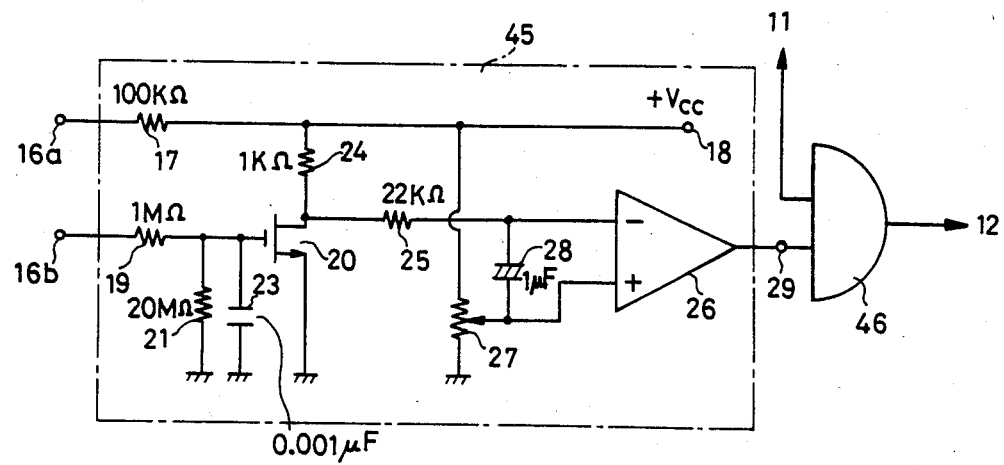
FIG. 6 is a detailed circuit diagram of a protection circuit 61 of the circuit of FIG. 2.

FIG. 6 shows one example of an actual circuit diagram of the protection circuit 45. The contact tip 16a is connected through a resistor 17 of 100 kΩ to the positive power source terminal 18. Another contact tip 16b is connected through a resistor 19 of 1MΩ to a gate electrode of a MOS-FET 20. The gate electrode is grounded by a parallel connection of a resistor 21 of 20MΩ and a capacitor 23 of 0.001 μF. The source of the MOS-FET 20 is grounded and the drain is connected through a resistor 24 of 1 kΩ to the positive power source terminal 18. The drain of the MOS-FET 20 is connected through a resistor 25 to a negative input terminal − of a differential amplifier 26. A potentiometer 27 is connected between the positive power source terminal 18 and the ground, and a sliding terminal of the potentiometer 27 is connected to a positive input terminal + of the differential amplifier 26. A capacitor 28 of a large capacitance for instance, 1 μF is connected across the negative input terminal − and the positive input terminal + of the differential amplifier 26. The output terminal 29 of the differential amplifier 26 is connected to an input terminal of an AND gate 46, the output of which is to be given to the input terminal of the counter circuit 12. In the circuit of FIG. 6, the resistor 19 and capacitor 23 form a low pass filter, and the resistor 25 and the capacitor 28 form another low pass filter. These low pass filters serve to eliminate spurious noise based on commercial power line current when the contact tip 16b only touches the skin, thereby avoiding misoperation.

When both contact tips 16a and 16b touch the human skin, then, the resistance between the contact tips becomes from 100 kΩ to several hundred MΩ, depending on the part of the body. That is the contact tips 16a and 16b are connected by the high resistance of the skin. Accordingly, a current flows from the power source terminal 18 through the resistor 17, contact tip 16a, the skin, contact tip 16b, the resistor 19 and the resistor 21 to the ground. Accordingly, a voltage is induced across the resistor 21 and the voltage is impressed on the gate electrode of the MOS-FET 20. Therefore, the MOS-FET 20 makes its drain current flow and the differential amplifier 26 amplifies change of its negative input terminal voltage, thereby issuing an output to the AND gate circuit 46. Therefore, when both contacts 16a and 16b touch the skin, the signal from the protection circuit 45 is introduced to the AND gate 46 to actuate the counter circuit 12 and hence the laser 4, to emit the laser light.

Instead of the above-mentioned proximity detection way, by utilizing the contact current conduction on the skin, another way of proximity detection, for instance by use of known capacitance change detection by the proximity of an electrode to the human skin may be similarly used.

What is claimed is:

1. An apparatus for laser light medical treatment comprising:
    a hand set casing, having an emission hole,
    laser light beam emitting means, including a source of laser light, being disposed within said hand set casing and for applying a laser light beam through said emission hole to a skin of a patient for medical treatment,
    proximity sensing means provided on both sides of and close to said emission hole for detection of a proximity of said emission hole to said skin of the patient, and
    switching means to cut off emission of said laser light beam when said proximity of said emission hole to said skin is not detected by said proximity sensing means.

2. An apparatus for laser light medical treatment in accordance with claim 1, wherein
    said proximity sensing means is a pair of electrodes disposed on both sides of said emission hole for electrical detection of proximity of skin to said electrodes.

3. An apparatus for laser light medical treatment in accordance with claim 2, wherein
    said proximity sensing means further comprises a detector means for detecting a change in a current passing between said electrodes.

4. An apparatus for laser light medical treatment in accordance with claim 2, wherein
    said proximity sensing means further comprises a detector means for detecting a change of a capacitance between said electrodes.

5. An apparatus for laser light medical treatment in accordance with claim 1, which further comprises
    timer means for controlling said laser light beam emission in a manner to be emitted for a desired set time period.

6. An apparatus for laser light medical treatment in accordance with claim 1, which further comprises
    time period indicating means for indicating remaining treating time period during the treating.

7. An apparatus for laser light medical treatment in accordance with claim 1, which further comprises
    warning means for warning when the laser light beam emitting means is in an emitting state.

8. An apparatus for laser light medical treatment in accordance with claim 7, wherein said warning means comprises
    a photoelectric element which issues a signal when receiving a back light of said laser light beam emitting means, and
    a switching means for cutting off power feeding to said laser light beam emitting means.

9. An apparatus for laser light medical treatment in accordance with claim 8, wherein
    said warning means is a sound producing means.

10. An apparatus for laser light medical treatment in accordance with claim 8, wherein
    said laser light emits invisible light and
    said warning means is a light emitting means which emits visible light.

11. An apparatus for laser light medical treatment in accordance with claim 7, wherein
    said warning means is a sound producing means.

12. An apparatus for laser light medical treatment in accordance with claim 7, wherein
    said laser light emitting means emits invisible light and
    said warning means is a light emitting means which emits visible light.

* * * * *